(12) United States Patent
Jönsson et al.

(10) Patent No.: US 6,616,949 B2
(45) Date of Patent: Sep. 9, 2003

(54) PROCESS FOR PRODUCING MICROPARTICLES

(75) Inventors: Monica Jönsson, Bara (SE); Timo Laakso, Campton (GB); Mats Reslow, Lund (SE)

(73) Assignee: Jagotec AG, Muttenz (CH)

( * ) Notice: Subject to any disclaimer, the term of this patent is extended or adjusted under 35 U.S.C. 154(b) by 0 days.

(21) Appl. No.: 09/970,796

(22) Filed: Oct. 5, 2001

(65) Prior Publication Data

US 2002/0086060 A1 Jul. 4, 2002

Related U.S. Application Data

(60) Provisional application No. 60/260,497, filed on Jan. 8, 2001.

(30) Foreign Application Priority Data

Nov. 16, 2000 (SE) ................................. 0004217

(51) Int. Cl.$^7$ ............................ B01J 13/02; A61K 9/50; A61K 47/30; B32B 15/02
(52) U.S. Cl. ................... 424/501; 424/502; 514/772.3; 264/4.1; 264/4.3; 264/4.33; 264/4.6; 428/402.21
(58) Field of Search ................................. 424/501, 502; 514/772.3; 264/4.1, 4.3, 4.33, 4.6; 428/402.21

(56) References Cited

U.S. PATENT DOCUMENTS

| | | |
|---|---|---|
| 3,691,090 A | 9/1972 | Kitajima et al. |
| 3,737,337 A | 6/1973 | Schnoring et al. |
| 3,881,991 A | 5/1975 | Kurimotor et al. |
| 4,389,330 A | 6/1983 | Tice et al. |
| 4,713,249 A | 12/1987 | Schröder |
| 5,407,609 A | 4/1995 | Tice et al. |
| 5,455,342 A | 10/1995 | Redding, Jr. |
| 5,470,582 A | 11/1995 | Supersaxo et al. |
| 5,578,709 A | 11/1996 | Woiszwillo et al. |
| 5,622,657 A | 4/1997 | Takeda et al. |
| 5,654,010 A | 8/1997 | Johnson et al. |
| 5,667,808 A | 9/1997 | Johnson et al. |
| 5,753,234 A | 5/1998 | Lee et al. |
| 5,776,885 A | 7/1998 | Orsolini et al. |
| 5,981,719 A | 11/1999 | Woiszwillo et al. |

FOREIGN PATENT DOCUMENTS

| | | |
|---|---|---|
| EP | 0 213 303 A2 | 3/1987 |
| EP | 0 540 582 B1 | 8/1994 |
| EP | 0 688 429 B1 | 2/1998 |
| EP | 0 330 180 B2 | 3/1999 |
| JP | 11302156 | * 11/1999 |
| WO | WO 90/13780 A1 | 11/1990 |
| WO | WO 93/21008 A1 | 10/1993 |
| WO | WO 94/12158 A1 | 6/1995 |
| WO | WO 96/10042 A1 | 4/1996 |
| WO | WO 97/14408 A1 | 4/1997 |
| WO | WO 99/00425 A1 | 1/1999 |
| WO | WO 99/20253 A1 | 4/1999 |

OTHER PUBLICATIONS

US 5,849,884, 12/1998, Woiszwillo et al. (withdrawn)

"Formation and Isolation of Spherical Fine Protein Microparticles Through Lyophilization of Protein—Poly(ethylene glycol) Aqueous Mixture", Takahiro Morita et al., Pharmaceutical Research, vol. 17, 11, 2000, pp. 1367 to 1373.

Protein encapsulation into biodegradable microspheres by a novel S/O/W encapsulation method using poly(ethylene glycol) as a protein micronization adjuvant, Takahiro Morita et al., Journal of Controlled Release, 69 (2000) pp. 435–444.

Artursson et al., "Characterizations of Polyacryl Starch Microparticles as Carriers for Proteins and Drugs," *Journal of Pharmaceutical Sciences*, vol. 73, No. 11, pp. 1507–1513, (1984).

Franssen et al., "A Novel Preparation Method for Polymeric Microparticles Without the Use of Organic Solvents," *International Journal of Pharmaceutics*, vol. 168, pp. 1–7 (1998).

Fu et al., "Visual Evidence of Acidic Environment Within Degrading Poly(lactic–co–glycolic acid) (PLGA) Microspheres" *Pharmaceutical Research*, vol. 17, No. 1, pp. 100–106 (2000).

Laakso et al., "Biodegradable Microspheres IV: Factors Affecting the Distribution and Degradation of Polyacryl Starch Microparticles," *Journal of Pharmaceutical Sciences*, vol. 75, No. 10, pp. 962–967 (1986).

Laakso et al., "Biodegradable Microspheres X: Some Properties of Polyacryl Starch Microparticles Prepared from Acrylic Acid–Esterified Starch," *Journal of Pharmaceutical Sciences*, vol. 76, No. 12, pp. 935–939 (1987).

Schröder, "Crystallized Carbohydrate Spheres as a Slow Release Matrix for Biologically Active Substances," *Biomaterials*, vol. 5, pp. 100–104 (1984).

Schröder, "Crystallized Carbohydrate Spheres for Slow Release and Targeting," *Enzymology*, vol. 112, No. 9, pp. 116–128 (1985).

(List continued on next page.)

Primary Examiner—Carlos A. Azpuru
(74) Attorney, Agent, or Firm—Burns, Doane, Swecker & Mathis, L.L.P.

(57) ABSTRACT

A process for producing microparticles containing biologically active substance, in which process an aqueous solution of the said substance is prepared, this solution is mixed with an aqueous solution of PEG such that the substance is concentrated and/or solidified, the substance is optionally washed, the substance is mixed with an organic polymer solution, the composition obtained is mixed, after the admixture of said polymer solution, with an aqueous polymer solution, thereby forming an emulsion of droplets of first mentioned polymer as the internal phase, said droplets are solidified into microparticles, the microparticles are dried and a release-controlling shell is optionally applied to these.

39 Claims, No Drawings

OTHER PUBLICATIONS

Stenekes et al., "The Preparation of Dextran Microspheres in an All–Aqueous System: Effect of the Formulation Parameters on Particle Characteristics," *Pharmaceutical Research*, vol. 15, No. 4 pp. 557–561 (1998).

Stjärnkvist et al., "Biodegradable Microspheres XIII: Properties of the Crosslinking Chains in Polyacryl Starch Microparticles," *Journal of Pharmaceutical Sciences*, vol. 78, No. 1, pp. 52–56 (1989).

Agersø et al., "Plasma Concentration of hGH and anti–hGH Antibodies After Subcutaneous Administration of hGH for 3 Weeks to Immunosuppressed Pigs," *J. Pharmacol Toxicol No. 41* pp. 1–8 (1999).

Johnson et al., "A Month–Long effect From a Single Injection of Microencapsulated Human Growth Hormone," *Nature Medicine*, vol. 2, No. 7 pp. 795–799 (1996).

Putney, "Encapsulation of Proteins for Improved Delivery," Current Opinion in *Chemical Biology*, Nol. 2, pp. 548–552 (1998).

"Clean Package Insert," Nutropin Depot (somatropin(rDNA origin) for injectable suspension, Genentech, Inc., 1 DNA Way, South San Francisco, CA 940–4990, pp. 1–6 (Dec. 13, 1999).

* cited by examiner

PROCESS FOR PRODUCING MICROPARTICLES

This application claims the benefit of Provisional Application No. 60/260,497, filed Jan. 8, 2001.

TECHNICAL FIELD

The present invention lies within the field of galenic formulations for the administration of biologically active substances, more specifically microparticles for controlled release primarily intended for parenteral administration of biologically active substances, especially drugs. More specifically, it relates to a novel production process for such particles containing a biologically active substance and to a novel process for converting a water-soluble protein into a concentrated and/or solidified form thereof.

BACKGROUND TO THE INVENTION

Many drugs have to be administered by injection, since they are either subjected to degradation or are insufficiently absorbed when they are given, for example, orally or nasally or by the rectal route. A drug preparation intended for parenteral use has to meet a number of requirements in order to be approved by the regulatory authorities for use on humans. It must therefore be biocompatible and biodegradable and all used substances and their degradation products must be non-toxic. In addition, particulate drugs intended for injection have to be small enough to pass through the injection needle, which preferably means that they should be smaller than 200 $\mu$m. The drug should not be degraded in the preparation to any great extent during production or storage thereof or after administration and should be released in a biologically active form with reproducible kinetics.

One class of polymers which meets the requirements of biocompatibility and biodegradation into harmless end products is the linear polyesters based on lactic acid, glycolic acid and mixtures thereof. These polymers will also hereinafter be referred to as PLGA. PLGA is degraded by ester hydrolysis into lactic acid and glycolic acid and has been shown to possess excellent biocompatibility. The innocuous nature of PLGA can be exemplified, moreover, by the approval by the regulatory authorities, including the U.S. Food and Drug Administration, of several parenteral delayed release preparations based on these polymers.

Parenterally administrable delayed release products currently on the market and based on PLGA include Decapeptyl™ (Ibsen Biotech), Prostap SR™ (Lederle), Decapeptyl® Depot (Ferring) and Zoladex® (Zeneca). The drugs in these preparations are all peptides. In other words, they consist of amino acids condensed into a polymer having a relatively low degree of polymerization and they do not have any well-defined three-dimensional structure. This, in turn, usually allows the use of relatively stringent conditions during the production of these products. For example, extrusion and subsequent size-reduction can be utilized, which techniques would probably not be allowed in connection with proteins, since these do not, generally speaking, withstand such stringent conditions.

Consequently, there is also a need for controlled release preparations for proteins. Proteins are similar to peptides in that they also consist of amino acids, but the molecules are larger and the majority of proteins are dependent on a well-defined three-dimensional structure as regards many of their properties, including biological activity and immunogenicity. Their three-dimensional structure can be destroyed relatively easily, for example by high temperatures, surface-induced denaturation and, in many cases, exposure to organic solvents. A very serious drawback connected with the use of PLGA, which is an excellent material per se, for delayed release of proteins is therefore the need to use organic solvents to dissolve said PLGA, with the attendant risk that the stability of the protein will be compromised and that conformation changes in the protein will lead to an immunological reaction in the patient, which can produce both a loss of therapeutic effect, through the formation of inhibitory antibodies, and toxic side effects. Since it is extremely difficult to determine with certainty whether a complex protein has retained its three-dimensional structure in every respect, it is very important to avoid exposing the protein to conditions which might induce conformation changes.

Despite intense efforts aimed at modifying the PLGA technology in order to avoid this inherent problem of protein instability during the production process, progress within this field has been very slow, the main reason probably being that the three-dimensional structures for the majority of proteins are far too sensitive to withstand the manufacturing conditions used and the chemically acidic environment formed with the degradation of PLGA matrices. The scientific literature contains a large number of descriptions of stability problems in the manufacture of microspheres of PLGA owing to exposure to organic solvents. As an example of the acidic environment which is formed upon the degradation of PLGA matrices, it has recently been shown that the pH value in a PLGA microsphere having a diameter of about 40 $\mu$m has been shown to fall to 1.5, which is fully sufficient to denature, or otherwise damage, many therapeutically usable proteins (Fu et al, Visual Evidence of Acidic Environment Within Degrading Poly(lactic-co-glycolic acid) (PLGA) Microspheres, Pharmaceutical Research, Vol. 17, No. 1, 2000, 100–106). Should the microspheres have a greater diameter, the pH value can be expected to fall further owing to the fact that the acidic degradation products then get more difficult to diffuse away and the autocatalytic reaction is intensified.

The technique which is currently most commonly used to encapsulate water-soluble substances, such as proteins and peptides, is the use of multiple emulsion systems. The drug substance is dissolved in an aqueous or buffer solution and subsequently mixed with an organic solvent, immiscible with water, containing the dissolved polymer. An emulsion is formed which has the aqueous phase as the inner phase. Different types of emulsifiers and vigorous mixing are often used to create this first emulsion. This emulsion is then transferred, under agitation, to another liquid, usually water, containing another polymer, for example polyvinyl alcohol, which produces a water/oil/water triple emulsion. The microspheres are then hardened in some way. The most common way is to utilize an organic solvent having a low boiling point, typically dichloromethane, and to distil off the solvent. If the organic solvent is not fully immiscible with water, a continuous extraction procedure can be used by adding more water to the triple emulsion. A number of variations of this general procedure are also described in the literature. In certain cases, the primary emulsion is mixed with a non-aqueous phase, for example silicone oil. Solid drug materials can also be used instead of dissolved ones.

PLGA microspheres containing proteins are described in WO-A1-9013780, in which the main feature is the use of very low temperatures during the production of the microspheres for the purpose of preserving high biological activity in the proteins. The activity for encapsulated superoxide dismutation is measured, but only on the part which has been released from the particles.

This method has been used to produce PLGA microspheres containing human growth hormone in WO-A1-9412158, wherein human growth hormone is dispersed in methylene chloride containing PLGA, the obtained dispersion is sprayed into a container of frozen ethanol beneath a layer of liquid nitrogen in order to freeze the fine droplets and said droplets are allowed to settle in the nitrogen on the ethanol. The ethanol is subsequently thawed and the microspheres start to sink in the ethanol, where the methylene chloride is extracted in the ethanol and the microspheres are hardened. Using this methodology, the protein stability can be better retained than in the majority of other processes for enclosing proteins in PLGA microspheres, and a product has also recently been approved by the registration authorities in the USA. However, this still remains to be clearly demonstrated for other proteins and the problem remains of exposing the enclosed biologically active substance to a very low pH during the degradation of the PLGA matrix.

In the aforementioned methods based on encapsulation with PLGA, the active substances are still exposed to an organic solvent and this, generally speaking, is harmful to the stability of a protein. Moreover, the discussed emulsion processes are complicated and probably problematical in any attempt to scale up to an industrial scale. Furthermore, many of the organic solvents which are utilized in many of these processes are associated with environmental problems and their high affinity for the PLGA polymer makes their removal difficult.

A number of attempts to solve the above-described problems caused by exposure of the biologically active substance to a chemically acidic environment during the biodegradation of the microsphere matrix and organic solvents in the manufacturing process have been described. In order to avoid an acidic environment during the degradation, attempts have been made to replace PLGA as the matrix for the microsphere by a polymer which produces chemically neutral degradation products, and in order to avoid exposing the biologically active substance to organic solvents, either it has been attempted to manufacture the microspheres in advance and, only once they have been processed and dried, to load them with the biologically active substance, or attempts have been made to exclude or limit the organic solvent during manufacture of the microspheres. A process for limiting the quantity of solvent used where polymers are used which can only be dissolved in organic solvents is described in WO 99/20253, in which the limitation is obtained by the use of an aqueous PEG solution to form an emulsion. In this publication, there is no discussion of any technique for concentrating or solidifying the biologically active substance to be incorporated in the microparticles.

WO 97/14408 describes the use of air-suspension technology for producing microparticles for sustained release after parenteral administration, without the biologically active substance being exposed to organic solvents. However, the publication provides no guidance towards the process according to the invention or towards the novel microparticles which can thereby be obtained.

In U.S. Pat. No. 5,470,582, a microsphere consisting of PLGA and containing a macromolecule is produced by a two-stage process, in which the microsphere as such is first manufactured using organic solvents and then loaded with the macromolecule at a later stage in which the organic solvent has already been removed. This procedure leads to far too low a content of the biologically active substance, generally 1–2%, and to a very large proportion being released immediately after injection, which very often is entirely unsuitable. This far too rapid initial release is already very high given a 1% load and becomes even more pronounced when the active substance content in the microspheres is higher. Upon the degradation of the PLGA matrix, the pH falls to levels which are generally not acceptable for sensitive macromolecules.

It is in many cases necessary or desirable to modify a biologically active substance, for example a drug, from soluble to solid form, for example in order to improve its stability and/or enable effective production of a formulation of the substance in question. For example, in an encapsulation procedure which utilizes an emulsifying operation, it can be necessary to use a solid form of the biologically active substance to obtain higher efficacy through the avoidance of transport to the outer phase, or the interface between the outer and inner phase, and in order to retain the biological activity of the substance. In connection with e.g. use of PLGA as a microparticle matrix there is thus a requirement for stabilizing the biologically active substance, both during the incorporation thereof into the microparticles and during the release stage after parenteral administration, and therefore, processes for the stabilization of e.g. macromolecules are extremely valuable. For substances which tolerate harsh manufacturing conditions, extrusion and grinding can be used, but for sensitive biologically active substances, such as proteins, it is a question in the vast majority of cases of acquiring the solid form through chemical complexing. A well known example of one such drug preparation on the market is crystalline insulin complex-bonded with zinc.

Thus it is well known that, for proteins and peptides, complex-bonding with divalent metal ions, preferably zinc, has long been utilized to convert the biologically active substance into solid form. Basically, it is not possible to form chemical complexes, e.g. with zinc, with all biologically active substances, and not all complex-forming agents are acceptable for parenteral administration. There are however a large number of drawbacks with such procedures. One drawback is the often complicated chemistry which, even in apparently simple cases, can require a significant amount of effort in order to be controlled and well-characterized. Another drawback is that the registration authorities in certain countries consider that even well known and marketed substances, after such complexing, are to be regarded as new chemical substances, which lead to demands for extensive and very expensive characterizations from the chemical, safety and clinical aspects. Further drawbacks are introduced when the active substance is to be converted into solid and dry form, since this often involves spraying and drying procedures which are equipment-intensive and in many cases can be complex. Many sensitive substances do not tolerate exposure to an air/water or air/organic-liquid interface or to those shear forces which are required in order to form the spray droplets. Neither is it unusual for problems in dispersing or resuspending the substance converted into solid form, after it has been dried, not to yield a usable result, for example owing to the fact that these particles attach to one another in such a way that they cannot be driven apart by the use of acceptable conditions. In many of these procedures, organic solvents are used which risk being harmful to sensitive biologically active substances and to staff coming into contact with the substances and have an adverse effect upon the environment.

U.S. Pat. No. 5,654,010 and U.S. Pat. No. 5,667,808 describe the production of a solid form of recombinant human growth hormone, hGH, through complexing with zinc in order to create an amorphous complex, which is then micronized through an ultrasound nozzle and sprayed down in liquid nitrogen in order to freeze the droplets. The liquid nitrogen is then allowed to evaporate at a temperature of −80° C. and the resultant material is freeze-dried. Apart from the fact that the procedure is complex and generally difficult to apply, it comprises a spraying procedure in which the biologically active substance is exposed to a water/air surface and in which the amorphous form of the protein which is formed is suspended in methylene chloride. Methylene chloride is an entirely undesirable organic solvent from a toxicological viewpoint, both for the patients and for the working staff.

A process for the production of parenterally administrable microparticles and having the following features would therefore be extremely desirable:

- a process which makes it possible to concentrate or solidify the biologically active substance to be incorporated without the use of chemical complexing and with retention of the biological activity of the substance;
- a process which makes it possible to concentrate or solidify the biologically active substance to be incorporated in a parenterally administrable preparation without exposure of the substance to air/water or air/organic solvent interfaces;
- a process which makes it possible to concentrate or solidify the biologically active substance to be incorporated in a parenterally administrable preparation, without the use of a spraying process or drying process;
- a process which makes it possible to avoid a reconstitution stage and/or resuspension stage of the biologically active substance from dry state without prior stabilization through incorporation in microparticles;
- a process which makes it possible to entrap sensitive, biologically active substances in microparticles with retention of their biological activity;
- a process by means of which a substantially fully biodegradable and biocompatible preparation can be produced, which is suitable for injecting parenterally;
- a process by means of which a parenterally injectable preparation having a size exceeding 20 µm and, preferably exceeding 30 µm, is produced for the purpose of avoiding phagocytosis of tissue macrophages and which simplifies processing of the same during manufacture;
- a process for the production of microparticles containing a biologically active substance, which microparticles can be used as intermediate product in the production of a preparation for controlled, sustained or delayed release;
- a substantially fully biodegradable and biocompatible microparticulate preparation which is suitable for injecting parenterally;
- a microparticulate preparation containing a biologically active substance and having a particle size distribution which is suitable for coating by means of air suspension technology and having sufficient mechanical strength for this purpose;
- a coated microparticulate preparation containing a biologically active substance, which preparation gives a controlled release after parenteral administration,

DESCRIPTION OF THE INVENTION

According to a first aspect of the present invention, there is provided a process for the production of microparticles. More specifically, it relates to the production of microparticles containing a biologically active substance and primarily intended for parenteral administration of said substance to a mammal, especially humans. Primarily, it is a question of the production of microparticles intended for injection. Since the microparticles are primarily intended for injection, it is preferably a question of the production of particles having a mean diameter within the range of 10–200 µm, usually 20–100 µm and especially 20–80 µm.

The expression "microparticles" is used in connection with the invention as a general term for particles of a certain size according to the art which is known per se. One type of microparticles is therefore constituted by microspheres, which have a substantially spherical form, whilst the term microparticle can in general include deviation from such a perfect spherical form. The term microcapsule, which is known per se, also falls within the expression microparticle according to the prior art.

More specifically the process according to the present invention comprises:

a) preparing an aqueous solution of the biologically active substance to be incorporated in the microparticles, b) mixing the solution obtained in step a) with an aqueous solution of polyethylene glycol (PEG) under such conditions that the biologically active substance is concentrated and/or solidified, c) optionally washing the concentrated and/or solidified biologically active substance obtained in step b), d) mixing the concentrated and/or solidified biologically active substance obtained in step b) or c) with a solution of a biodegradable polymer in an organic solvent, e) mixing the composition obtained in step d) with an aqueous solution of a polymer having the ability of forming an emulsion, so as to form an emulsion of droplets of said biodegradable polymer, which contain the biologically active substance as the inner phase in an outer phase of said polymer solution, f) causing or allowing the droplets obtained in step e) to solidify into microparticles, g) drying the microparticles from step f), and h) optionally applying a release-controlling shell of a biocompatible and biodegradable polymer to the dried microparticles from step f).

Even though it is generally possible to incorporate biologically active substances in microparticles in a highly effective manner, since the biologically active substance is present in soluble form during the entrapment stage, it is in certain cases preferable for the biologically active substance to be converted into solid form. For example, it can be a matter of further stabilizing the biologically active substance during the entrapment stage, which is especially valuable for sensitive macromolecules exposed to organic solvents, of further increasing the yield or the load by converting the substance into a form which, after mixing with the inner phase (the polymer solution), cannot be distributed out in the outer phase or to the interface between the inner and outer phases, or of converting the substance into a form which is as inert as possible during the manufacture of the microparticles, this so that improved properties shall be acquired, for example, in terms of the size distribution of the microparticles.

It has thus very surprisingly been found that PEG, which is often used as the polymer to create the outer phase in a two-phase aqueous system, can also be used to concentrate and/or solidify the biologically active substance which is to be entrapped, and that this can be realized under mild conditions which can preserve, for example, the three-dimensional conformation and biological activity of a protein.

This process has a number of advantages compared with the prior art. In the first place, it is not necessary to complex-bond the biologically active substance, preferably a protein or a peptide, in order to obtain the concentration/solidification. In the second place, the use of this process often also produces better stability during the incorporation in the microparticles, compared with soluble protein. The fact that the process does not comprise a spraying or drying process before the biologically active substance is incorporated in the microparticles also means that exposure of the biologically active substance to high shearing forces and to interfaces (air/water or air/organic solvent) is avoided. Aggregation owing to electrostatic charges, something which is very common for small, dry particles, is also avoided. Any problems with wetting and resuspension of a dry powder of the biologically active substance can also be avoided. In purely general terms, spraying processes are also complex and poorly controlled. Neither is it necessary to utilize process steps such as freezing and slow thawing in order to convert the biologically active substance into dry form. It is also a distinct advantage that no organic solvents are used to convert the biologically active substance to the concentrated/solidified form.

For step a) of the process according to the invention, the aqueous solution of the biologically active substance is prepared by means of methods which are well known within the field and which do not need here to be described in further detail. However, fundamental to this is that the solution is prepared under such mild conditions, primarily in terms of temperature and agitation, that the bioactivity of the biologically active substance is preserved. Within the field, moreover, well-known buffer substances which are acceptable for parenteral use are often used to control or regulate the pH value of the solution. Where required, substances which are well known within the field and are acceptable for parenteral use can also be used, for example to adjust ionic strength and osmolarity. When so desired, the obtained solution can be sterilized by means of, for example, sterile filtration.

Through the use of the aqueous solution of polyethylene glycol in step b), a concentration of the biologically active substance, for example a protein, can be obtained. This concentration often results in the biologically active substance precipitating out, i.e. forming a precipitation, solid particles thereby being formed. This can be detected, for example, by examination with a light microscope. Since the process is often carried out quickly, the structure of the particles is generally amorphous. Other forms of particles, for example crystals and supercooled glass, are also covered by the invention, however, depending on how the process is carried out.

The term "is concentrated" also however covers the case in which the biologically active substance does not precipitate, but merely forms a more or less highly viscous solution. The term "is solidified" thus also covers the case in which a highly viscous solution of this kind forms such stable droplets that, in practice, it can be handled and incorporated in microparticles in substantially the same way as if it were a precipitation. The concentrated/solidified biologically active substance can be found in the microparticle matrix in the form of islands or discrete particles.

One embodiment of the process according to the invention is thus represented by the case in which step b) is performed such that the solidification of the biologically active substance leads to a precipitation of the same.

In another embodiment, step b) is performed such that the solidification of the biologically active substance results in a highly viscous solution, which has the ability of forming droplets which can be handled at room temperature.

In a further embodiment of the process, step b) is performed to form a reversibly solidified active substance.

In yet another embodiment of the process, the solidified biologically active substance forms a pellet or a highly viscous or solid bottom phase in centrifugation or ultracentrifugation.

By "reversibly solidified" is meant, in general terms, that the biologically active substance in question, when dissolved in a medium suitable for each unique biologically active substance and under suitable conditions, and/or when released from the microparticles in vitro and/or in vivo, is restored to essentially the same form, both chemically and biologically, as it had prior to the concentration/solidification with polyethylene glycol.

That the solidified biologically active substance forms a pellet or a highly viscous or solid bottom phase in centrifugation or ultracentrifugation provides a means of detecting the desired concentration/solidification. This means, moreover, that the substance in question is present in another physical form than the soluble form which is present in step a) after the preparation of the aqueous solution.

That the biologically active substance is present in concentrated form means, in general terms, that it is present in a concentration which exceeds the concentration obtainable when the substance in question is dissolved in an aqueous medium, with or without stabilizers and solubility-promoting substances, and with the retention of biological activity and chemical stability.

A combination of molecular weight and concentration of the PEG such that the desired concentration and/or precipitation of the biologically active substance is obtained should be chosen. Such conditions can simply be tried out for each specific biologically active substance as they will be dependent on the properties of the biologically active substance, for example molecular weight and solubility. The molecular weight of the PEG can be in the range of 400–100,000 Daltons, more preferably 4000–35000 Daltons, even more preferably 6000–20,000 Daltons, and most preferably 20,000 Daltones. The concentration of the PEG can be in the range of 1–50%, preferably 2–45%, more preferably 10–40% and most preferably 20–35%. That a concentration and/or precipation has been obtained can be investigated as above. That the biologically active substance has retained its bioactivity is most easily measured at this stage by dilution, for example in a suitable buffer solution, and chemical analysis of the biologically active substance, or alternatively by suitable immunological and/or animal assays. If unsatisfactory results are obtained in the initial trials adjustment of pH, the buffer substance, or buffer substances used, and their concentration, temperature and/or inclusion of stabilizers known in the art should be investigated, as well as a change in the concentration and mean molecular weight of the PEG used, such adjustments being readily available to anyone skilled in the art. This step may obviously also be performed under an inert atmosphere to avoid oxidation reactions, the simplest way being to purge the oxygen in the solution by an inert gas, like nitrogen or helium. For extremely sensitive substances it may be necessary to use a very pure PEG to avoid, for example, oxidation reactions.

The extent to which step c) of the process according to the invention needs to be executed or not, i.e. whether the obtained concentrated and/or solidified active substance should be washed and, if so, to what extent, has to be determined in each individual case and depends, inter alia, on the proportion of the biologically active substance which is present in dissolved form in the PEG solution, on whether the dissolved substance is sufficiently stable in this form to be able to be incorporated in the microparticles without far too large a quantity of undesirable degradation products being formed, on the effect which this dissolved substance has on the manufacture of the microparticles, on whether other conditions are required to be used, for example in terms of the concentration and average molecular weight of ERG, as well as pH and ionic strength, than those employed in step b), on whether PEG constitutes a stabilizer for the biologically active substance per se or by retaining the substance in undissolved form or preventing adsorption to surfaces.

The actual washing of the concentrated and/or solidified active substance can be effected by means of suitable techniques established within this technical field. In the simplest form of all, centrifugation washes can be Used and in many cases filtration can also be used. In the latter case, conditions are preferably employed under which the concentrated and/or solidified active substance is not allowed to dry, since this can lead, for example, to aggregation, and the process time is shortened by the application of pressure. Fundamental to this, of course, is that the liquid which is used must not dissolve the concentrated and/or solidified active substance and that the conditions which are suitable should be determined for each individual biologically active substance. In many cases, conditions can be chosen, in terms of buffer composition, additives and temperatures, such that this requirement is met, and necessary information can be obtained from the literature or via simple experiments. Naturally, polymers can be added to avoid dissolution of the concentrated and/or solidified active substance and, in the simplest case of all, the same composition of the PEG solution is used as when the concentration/solidification was carried out. This step can also be performed under an inert atmosphere and at a low temperature.

As to the mixing step d) there are many suitable methods in the art for carrying out such an encapsulation step, for example those described in EP 0 330 180, U.S. Pat. No. 3,737,337, U.S. Pat. No. 3,691,090, WO 99/20253, U.S. Pat. No. 4,389,330, U.S. Pat. No. 5,407,609 and U.S. Pat. No. 5,622,657. Of these WO 99/20253 and U.S. Pat. No. 5,622,657 are preferred.

The biodegradable polymer used in step d) can be selected in accordance with previously known art per se, i.e. among polymeric materials which are previously known as matrix materials for microparticles, provided that the polymer in question is soluble in an organic solvent (hereby for instance starch is excluded) and biocompatible, i.e. biologically acceptable.

Especially, however, a homo or copolymer containing L-hydroxy acid units is preferred, preferably lactic acid and/or glycolic acid, e.g. PLGA.

Preferably the polymer has an average molecular weight in the range of 2–200 kDA, more preferably 2–110 kDA.

For the mixing operation in step d), a weight ratio of biodegradable polymer:biologically active substance within the range of 3:1 to 10,000:1 is expediently used.

As has been discussed above, it is also the case for the mixing operation that the active substance is concentrated/solidified with the use of a PEG solution before being mixed with the polymer solution. It is possible to add the polymer solution to the biologically active substance or vice versa. After this, a homogeneous distribution of the concentrated/solidified active substance in the polymer solution is created by means of a suitable technique. Such a technique is well known within the field, examples which might be quoted being magnetic agitation, propeller agitation or the use of one or more static mixers.

Regarding the polymer used in step e) for the purpose of forming an emulsion, information is published, within precisely this technical field, on a large number of polymers with the capacity to form such emulsions. All such polymers must be considered to lie within the scope of the present invention. An especially suitable polymer in this context, however, is polyethylene glycol. The molecular weight of said polyethylene glycol generally is within the range of about 1 to 40 kDa, preferably 5 to 35 kDa. Dependent on said molecular weight and the properties of the active substance to be encapsulated, the concentration of the polyethylene glycol is adjusted so as to be in the range of 20–80% (w/w), preferably 20–60% (w/w), such as 30–55% (w/w) or 30–50% (w/w). In other words, a relatively high PEG concentration is used in the outer phase such that a stable emulsion is obtained and diffusion of active ingredient from the droplets/particles is prevented. An evaluation of the optimum concentration can be made by experiments which are relatively simple to perform for a person skilled in the art.

The mixing operation in step e) can be performed in many different ways, for example through the use of propeller agitation or at least one static mixer. The mixing is normally carried out within the temperature range of 4–50° C., preferably 20–40° C., often about 37° C. In a batch process, the solution of the first polymer can be added to the second polymer solution or vice versa. Where static mixers or blenders are utilized, the operation is expediently executed by the two solutions being pumped in two separate pipelines into a common pipeline containing the blenders.

The emulsion can be formed using low shearing forces. In most cases, magnetic or propeller agitation is sufficient. On a larger scale, for example when the quantity of microparticles to be produced exceeds 50 g, it is expedient to use so-called baffles to obtain even more effective agitation in the container which is used. An alternative way of forming the emulsion is to use at least one static mixer, the organic polymer solution expediently being pumped at regulated speed in a pipe in which the static mixers have been placed. The pumping can be effected with any type of suitable pump, provided that it gives an even flow rate under these conditions, does not expose the mixture to unnecessarily high shearing forces and is acceptable for the manufacture of parenteral preparations in terms of purity and non-leakage of unwanted substances. In those cases, too, in which static mixers are used to create the emulsion, it is generally advantageous to have the solidification into microparticles take place in a vessel with suitable agitation.

A preferred embodiment of the process according to the invention means that in step e) the polymer solution is added to the composition in at least two stages, in which an addition is effected after the emulsion has been created or has begun to be created.

It is also within the scope of the present invention, of course, to add the polymer solutions in many stages and to change, for example, the average molecular weight and/or concentration of the polymer used.

The mixing operation in step e) is expediently performed, moreover, under such conditions that the formed droplets acquire the size required for the microparticles, i.e. preferably a mean diameter, in the dry state, within the range of 10–200 $\mu$m, more preferably 20–100 $\mu$m and most preferably 20–80 $\mu$m. However, also other previously known methods for the solidification of the microparticles are within the scope of the invention.

In connection with the solidification of the microparticles, it is important that this should take place under conditions which are mild for the incorporated biologically active substance(s). In other words, it is primarily a question of using a temperature which is not harmful to the current substance.

Confirmation that the chosen conditions are correct or appropriate can be obtained by establishing that the microparticles have a desired size distribution, are stable during the subsequent washing and drying operations and are dissolved substantially completely in vitro and/or that the incorporated substance has been encapsulated effectively and has retained bioactivity. The last-mentioned is usually examined using chromatographic methods or using other methods established within the art, in vitro or in vivo, after the microparticles have been dissolved.

The formed microparticles are preferably washed in a suitable manner in order to remove the outer phase and any surplus of active substance. Such washing is expediently effected by filtration, which is made possible by the good mechanical stability and suitable size distribution of the microparticles. Washing by means of centrifugation, removal of the supernatant and resuspension in the washing medium may often also be appropriate. In each washing process, one or more suitable washing media are used, which generally are buffer-containing aqueous solutions. In this connection, sifting can also be used, if required, in order to adjust the size distribution of the microparticles, for example to eliminate the content of too small microparticles and to ensure that no microparticles above a certain size are present in the finished product.

The microparticles can be dried in any way appropriate, for example by spray-drying, freeze-drying or vacuum-drying. Which drying method is chosen in the individual case often depends on what is most appropriate for the retention of the biological activity for the enclosed biologically active substance. Process considerations also enter into the picture, such as capacity and purity aspects. Freeze-drying is often the preferred drying method, since, correctly designed, it is especially mild with respect to the enclosed biologically active substance. That the incorporated biologically active substance has retained its bioactivity can be established by means of analysis appropriate to the substance after the substance has been dissolved under mild conditions.

In order to modify the release properties of the microparticles, a release-controlling shell made from a biocompatible and biodegradable polymer might also be applied, moreover. Examples of suitable polymers in this context are found in the prior art, and polymers of lactic acid and glycolic acid (PLGA) can especially be mentioned. The shell in question is preferably applied using air suspension technology. An especially suitable technique of this kind is described in WO97/14408 and details in this regard can thus be obtained from this publication, the content of which is included in the text by reference. The microparticles which are obtained by means of the process according to the present invention are extremely well suited to be coated by means of the said air suspension technology, and the coated microparticles obtained are especially well suited to parenteral administration.

When the produced microparticles are used, either they are coated with a release-controlling outer shell or not, the dry microparticles are suspended in a suitable medium, specifically to permit injection. Such media and processes in these regards are well known within the art and will not need here to be described in further detail. The actual injection can be given through a suitable needle or with a needle-free injector. It is also possible to inject the microparticles using a dry powder injector, without prior resuspension in an injection medium.

Apart from the advantages which have been discussed above, the process according to the invention has the advantage that the yield of the biologically active substance is generally high, that it is possible to obtain a very high active substance content in the microparticles whilst retaining the bioactivity of the substance, that the obtained microparticles have the correct size distribution for use for parenteral, controlled (for example delayed or sustained) release, since they are too large to be phagocytized by macrophages and small enough to be injectable through small needles, for example 23 G-25 G.

The process according to the invention is especially interesting in connection with proteins, peptides, polypeptides, polynucleotides and polysaccharides or, in general, other drugs or biologically active substances which are sensitive to or unstable in, for example, organic solvents. Recombinantly produced proteins are a very interesting group of biologically active substances. Generally speaking, however, the invention is not limited to the presence of such substances, since the inventive concept is applicable to any biologically active substance which can be used for parenteral administration. Apart from in connection with sensitivity or instability problems, the invention can thus also be of special interest in such cases where it would otherwise be difficult to remove solvent or where toxicological or other environmental problems might arise.

Examples of biologically active substances of the above-specified type are growth hormone, erythropoietin, interferon ($\alpha$, $\beta$, $\gamma$-type), vaccine, epidermal growth hormone, Factors IV, V, VI, VII, VIII and IX, LHRH-analogue, insulin, macrophage-colony-stimulating factor, granulocyte-colony-stimulating factor and interleukin.

Usable biologically active substances of the non-protein drug type can be chosen from the following groups:

Antitumour agents, antibiotics, anti-inflammatory agents, antihistamines, sedatives, muscle-relaxants, antiepileptic agents, antidepressants, antiallergic agents, bronchodilators, cardiotonic agents, antiarrhythmic agents, vasodilators, antidiabetics, anticoagulants, haemostatic agents, narcotics and steroids.

In connection with the invention the term biodegradable means that the microparticles, after parenteral administration, are dissolved in the body to form endogenic substances, ultimately for example lactic acid. The biodegradability can be determined or examined through incubation with any suitable medium in vitro. The biodegradability can also be examined through parenteral injection of the microparticles, for example subcutaneously or intramuscularly, and histological examination of the tissue as a function of times Normally, biodegradable microparticles from for instance PLGA dissapear from the tissue within a few weeks or months.

The biocompatibility can also be examined through parenteral administration of the microparticles, for instance subcutaneously or intramuscularly, and histological evaluation of the tissue, it being important to bear in mind that the biologically active substance, which often is a protein, has in itself the capacity to induce for instance an immunodefense if administered to another genus. For example, a large number of recombinantly produced human proteins can give rise to an immun response in test animals.

Those microparticles which are obtained when using the process according to the invention are suitable for parenteral administration, preferably via injection, to a mammal, especially a human being.

The microparticles obtained essentially consist of a parenterally administrable, biodegradable polymer as the matrix, which in turn contains the biologically active substance in essentially non-chemically complex-bonded form and in the form of solid particles having a mean size within the range of 0.05–30 μm.

By mean size is usually meant, in this context, mean diameter, at least in the case of spherical or substantially spherical particles. In another configuration, reference is generally to the mean value for the largest extent of the particle in any direction.

According to one alternative, the particles of the biologically active substance are obtained by precipitation, i.e. are present in precipitated form.

The solid particles preferably have a mean size within the range of 0.2–10 μm, more preferrably 0.5–5 μm, and most preferably 1–4 μm.

Preferably, the biodegradable polymer is a homo or copolymer containing α-hydroxy acid units. Said α-hydroxy acid is preferably lactic acid and/or glycolic acid, Preferably, the microparticles also have a release-controlling shell of the type discussed in connection with the process. Reference is also made to the process regarding preferred variants of the said shell.

However, an interesting alternative is represented by the case where the release-controlling shell has another polymer composition than the matrix.

Other microparticles obtainable by the process are those in which the bioactivity of the biologically active substance is at least 80%, preferably at least 90% and most preferably essentially maintained compared with the bioactivity exhibited by the substance prior to its incorporation in the polymer, Others still are those which are biodegradable and are eliminated from tissue after subcutaneous or intramuscular administration. The biologically active substance is preferably a protein and more preferably a recombinantly produced protein.

The protein is preferably chosen from amongst growth hormones, colony-stimulating factors, erythropoietines, interferons and vaccines.

More preferably the protein is a growth hormone, especially a human growth hormone (hGH).

That the biologically active substance in the polymer matrix is present in essentially non-chemically complex-bonded form means in general that the molecular ratio of total metal cations:biologically active substance is less than 0.2:1.

According to prior technique, it is primarily zinc which has been utilized for complex-bonding in similar context. Thus, the microparticles obtained have the advantage that they are essentially or wholly lacking in such zinc.

More preferably, the abovementioned molecular ratio of metal cations:biologically active substance is less than 0.1:1, especially less than 0.01:1, and most peferably, of course, as close to 0 as possible.

Where a human growth hormone constitutes the biologically active substance, this is preferably of the type whose dimers content is less than 2% by weight, and more preferably less than 1% by weight, and whose polymers content is less than 0.2% by weight, preferably less than 0.1% by weight.

Microparticles which form a parenterally administrable, biodegradable microparticle preparation containing a biologically active substance which, during the first 24 hours after injection, has an active substance release which is less than 30% of the total release, determined from a concentration-time graph in the form of the ratio between area under the curve during the first 24 hours and total area under the curve in question.

Preferably, the release during the first 24 hours after the injection is less than 20%, more preferably less than 15%, even more preferably less than 10% and most preferably less than 5%, of the total release.

Microparticles which produce a microparticle preparation of the abovementioned type, which, during the first 48 hours after injection, has an active substance release in which the maximum concentration in plasma or serum is less than 300% of the maximum concentration of the biologically active substance during any point in time in excess of 48 hours after injection.

The said maximum concentration is preferably less than 200% and more preferably less than 100% of the maximum concentration in question.

Another example is a microparticle preparation of the abovementioned type, which has a biologically active substance release in which the bioavailability of the said substance is at least 35% of the bioavailability obtained when the substance in question is injected intravenously in soluble form.

The said bioavailability is preferably at least 45%, more preferably at least 50%, of the bioavailability obtained when the biologically active substance is injected intravenously.

A further example is a microparticle preparation of the said type which has an active substance release characterized in that, in the release occurring during any continuous seven-day period, the quotient of the highest concentration of the biologically active substance in serum or plasma divided by the mean concentration during the said seven-day period is less than 5, provided that the chosen seven-day period does not include the first 24 hours after injection.

The said release is preferably less than 4 times, more preferably less than 3 times, and most preferably less than 2 times, Another microparticle preparation which can be obtained by means of the process according to the invention has a biologically active substance release in which the mean residence time for the substance in question is at least 4 days.

Preferably, the said mean residence time is at least 7 days, more preferably at least 9 days, for example at least 11 days, or especially at least 13 days.

The features which have been specified for the above-presented microparticle preparations can be combined in any suitable combinations whatsoever.

The different characteristics specified for the microparticle preparation above primarily relate to the terms MRT, burst and bioavailability.

These can be defined as follows:

MRT

An object of preparations for controlled release is to obtain a sustained release of the active material. One measure which can be used to quantify the release time is mean residence time (MRT), which is the recognized term within pharmacokinetic.

MRT is the average time for which the molecules introduced into the body reside within the body. (Clinical Pharmacokinetics. Concepts and Applications. Malcolm Rowland and Thomas N. Tozer, $2^{nd}$ ed., Lea & Febiger, Philadelphia London).

The MRT value can be calculated from plasma concentration data, using the following formula.

$$MRT = \frac{\int_0^\infty tC\,dt}{\int_0^\infty C\,dt}$$

where C is the plasma concentration and t is the time.

Burst

A common problem with controlled release preparations for parenteral use is that a large part of the drug is released during the early phase immediately following administration in the body. Within the specialist literature, this is termed the "burst effect". This is generally due to the fact that the drug is located on the surface of the formulation or that the formulation (which can consist of microparticles) bursts. A low burst effect is very desirable, since a high concentration of drug can be toxic and the part which disappears rapidly in the initial period, moreover, is poorly utilized, which means that more drug is required to maintain a therapeutic level of the drug during the intended treatment period.

Burst is defined as that fraction of the drug which is absorbed during the first 24 hours of the total fraction which is absorbed.

In mathematical terms, it can be defined using "area under curve" calculations from plasma concentration graphs.

$$Burst = \frac{\int_0^{24h} C\,dt}{\int_0^\infty C\,dt} \cdot 100\%$$

Bioavailability

Bioavailability is a measure of how large a part of the supplied drug is absorbed in active form from the site of administration to the blood. Bioavailability is often compared with data from intravenous supply of the drug, in which there are therefore no absorption barriers, and is then referred to as absolute bioavailability.

Absolute bioavailability is defined according to the following formula:

$$F = \frac{AUC_x \cdot D_{iv}}{D_x \cdot AUC_{iv}}$$

where $AUC_x$ is the area-under-the-curve value for the examined formulation, $AUC_{xi}$ is the area-under-the-curve value for an intravenous supply of the drug, $D_x$ is the dose of the drug in the formulation and $D_{iv}$ is the intravenous dose.

The determination of the release profile and the pharmacokinetic parameters is preferably realized through animal trials. The most relevant species, owing to its similarity to humans, is the pig. Where the biologically active substance can induce, during the test, an immune response which threatens to affect the determination of the pharmacokinetic parameters for the biologically active substance, inhibition of the immune response should be used, for example by drug treatment. This is known within the technical field, and details can be obtained from the scientific literature, for example Agersö et al, (J. Pharmacol Toxicol 41 (1999) 1–8).

Other interesting microparticles are those which are biodegradable in vitro in the presence of alpha-amylase and/or amyloglucosidase, Further preferred microparticles are those which are biodegradable and are eliminated from tissue after subcutaneous or intramuscular administration, As regards the determination of the biological activity of the microparticles containing active substance, this must be carried out in a manner appropriate to each individual biological substance. Where the determination is effected in the form of animal trials, a certain quantity of the biologically active substance incorporated in the microparticles is injected, possibly after these microparticles have been previously dissolved under mild conditions, and the biological response is compared with the response obtained after injection of a corresponding quantity of the same biologically active substance in a suitable solution. Where the evaluation is made in vitro, for example in test tubes or in cell culture, the biologically active substance is preferably made fully available before the evaluation by the microparticles being dissolved under mild conditions, after which the activity is determined and compared with the activity for a control solution having the same concentration of the biologically active substance in question. In any event, the evaluation shall include any non-specific effects of the degradation products of the microparticles.

Finally, as can be gathered from the above-mentioned, another interesting aspect of the invention is represented by a process for converting a protein, or in general any other biologically active substance that is sensitive to or unstable in organic solvents, into a concentrated and/or solidified form thereof, which process comprises mixing an aqueous solution of said substance with an aqueous solution of polyethylene glycol (PEG) under such conditions that the protein is concentrated and/or solidified.

As to details and preferable embodiments of such conditions reference is made to the corresponding passages in connection with the process for producing microparticles. Thus, especially such details can be found in connection with the disclosure of step b) of last-mentioned process. Therefore, they need not be repeated here.

From the above-mentioned disclosure of the inventive idea it can, however, also be gathered that the process for converting a water-soluble protein into a concentrated and/or solidified form therof is also preferably performed in the absence of any freezing or lyophilization operation and/or in the absence of any organic solvent and/or in the absence of any spraying operation.

EXAMPLES

The invention will now be further illustrated by the non-limiting illustrative embodiments below.

Example 1

Procedure for the production of highly concentrated/precipitated hGH suitable for immobilization with PEG.

To 343 mg hGH are added 10 mM sodium phosphate buffer, pH 6.4, to a total volume of 2.5 ml. PEG with a average molecular weight of 20,000 D is dissolved in the same buffer to a concentration of 30%, the pH being adjusted to about 6.4. The PEG solution (25 ml) is poured into a beaker having a propeller, after which the temperature is adjusted to 15° C. and the hGH solution (about 1.25 ml) is added under propeller agitation and the mixture allowed to stand for 75 min. under continued agitation. The obtained suspension is centrifuged in a Sorvall SS34 (20 min. at 5,000 rpm). The supernatant is carefully drawn off. The precipitated protein can be washed once with sodium acetate, pH 6.4, containing 2 mM zinc acetate (10 ml) and the obtained supernatant is drawn off.

Example 2

Procedure for the encapsulation of PEG-concentrated/solidified hGH in PLGA (poly-DL-lactide-coglycolide).

Firstly, a polymer solution is prepared by dissolving 0.46 g of PLGA (RG504H, Boehringer Ingelheim) in 3 ml of ethyl acetate in a test tube. Then 44 mg of PEG-concentrated/solidified hGH manufactured in accordance with Example 1 is added to the polymer solution and is homogenously dispersed in said polymer solution by swirl mixing (VF2, IKA-WERK) for one minute. The dispersion is placed in a 5 mL syringe having a 18 G needle.

A 500 mL beaker containing 300 mL of 40% (w/w) polyethylene glycol 20,000 is provided with a propeller mixer having 4 blades. The hGH/polymer dispersion is transformed into the beaker by injecting the same slowly into the PEG solution. The agitation speed is then reduced and the admixture is allowed to stand during the night.

The agitation speed is again set to 8, and thereafter 400 mL of deionized water is added in order to reduce the viscosity to enable a filtering operation. The dispersion is then filtered while using a Millipore membrane filter, type DV, pour size 0.65 $\mu$m, washed with water (3×300 mL) and dried at vacuum during the night.

The microparticles thus obtained are then subjected to an experiment concerning release in vitro in 30 mM sodium phosphate, pH 7.4, at 37° C. with intermitent agitation. The studies are performed by suspending 40 mg of microspheres in 1.5 mL of buffer. At specific times 1 mL allequotes of said buffer are removed and replaced by fresh buffer. The results show that the release of the protein is sustained for several weeks.

Example 3

Procedure for coating of microspheres containing PEG-concentrated hGH.

The hGH-containing microspheres obtained in Example 2 are coated with a release-controlling shell made from PLGA by means of air suspension technology according to WO97/14408 with the use of a mixture consisting of 75% RG502H and 25% RG756 (both from Boehringer Ingelheim). After the coating operation, the coating is dissolved with a mixture of methylene chloride and acetone in a ratio of 1:3 and, after these solvents have been washed away, for example by repeated centrifugation, the microspheres are dissolved. The hGH content is determined, for example by analysis with high-pressure-liquid chromatography. The dimer and polymer contents of the protein are also determined using the same technique. The protein content can be around 11 percent by weight. The share of the protein which is present in the form of dimers is <2% and in the form of polymers <0.1%. The release kinetics for hGH from the coated microspheres can be determined in vitro and are characterized by the absence of an undesirable burst and otherwise by a continuous and regular release with a duration of around one week. With this process, parenterally administrable microspheres can thus be produced so as to be suitable for controlled release of hGH.

Example 4

Procedure for the production of highly concentrated/precipitated hGH suitable for immobilization with the use of PEG.

Precipitated hGH is produced according to Example 1, with the change that the precipitate is washed in histidine buffer, pH 4.9.

What is claimed is:

1. A process for producing parenterally administrable microparticles containing a biologically active substance, which process comprises:
   a) preparing an aqueous solution of the biologically active substance to be incorporated in the microparticles,
   b) concentrating the biologically active substance into a highly viscous solution thereof, which has the ability of forming droplets which can be handled at room temperature, or into a precipitation thereof in the form of solid particles, by a mixing of the solution obtained in step a) with an aqueous solution of polyethylene glycol (PEG),
   c) optionally washing the concentrated and/or solidified biologically active substance obtained in step b),
   d) mixing the concentrated and/or solidified biologically active substance obtained in step b) or c) with a solution of a biodegradable polymer in an organic solvent,
   e) mixing the composition obtained in step d) with an aqueous solution of a polymer having the ability of forming an emulsion, so as to form an emulsion of droplets of said biodegradable polymer, which contain the biologically active substance as the inner phase in an outer phase of said polymer solution,
   f) causing or allowing the droplets obtained in step e) to solidify into microparticles,
   g) drying the microparticles from step f), and
   h) optionally applying a release-controlling shell of a biocompatible and biodegradable polymer to the dried microparticles from step f).

2. A process according to claim 1, in which step b) is performed to a reversibly solidified active substance.

3. A process according to claim 1, in which the solidified biologically active substance forms a pellet or a highly viscous or solid bottom phase in centrifugation or ultracentrifugation.

4. A process according to claim 1, in which the polyethylene glycol used in step b) has an average molecular weight of 400–100,000 Da.

5. A process according to claim 1, in which the concentration of the polyethylene glycol used in step b) is in the range of 1–50% (w/w).

6. A process according to claim 1, in which the polymer is a homo or copolymer containing $\alpha$-hydroxy acid units.

7. A process according to claim 6, in which the $\alpha$-hydroxy acid is lactic acid and/or glycolic acid.

8. A process according to claim 1, in which in step d) a biocompatible and biodegradable polymer is utilized, which has an average molecular weight within the range of 2–200 kDA.

9. A process according to claim 1, in which in step d) a composition is formed in which the weight ratio between polymer and biologically active substance lies within the range of 3:1 to 10,000:1.

10. A process according to claim 1, in which in step e) the polymer solution is added to the composition in at least two steps, at least one of the additions being effected after the emulsion has begun to be created.

11. A process according to claim 1, in which in step e) polyethylene glycol is used as the aqueous polymer.

12. A process according to claim 11, in which the polyethylene glycol has an average molecular weight of 1–40 kDA.

13. A process according to claim 1, in which in step e) polymer droplets are formed which give the size required for the microparticles, in the dry state, within the range of 10–200 $\mu$m.

14. A process according to claim 13, in which after step e) the microparticles are washed, through filtration, and optionally sieved in order to obtain the desired particle size distribution.

15. A process according to claim 1, in which the drying in step g) is performed in the form of spray-drying, freeze-drying or vacuum-drying, preferably freeze-drying.

16. A process according to claim 1, in which, as the biologically active substance, a substance is incorporated which is selected from the group consisting of proteins, peptides, polypeptides, polynucleotides and polysaccharides.

17. A process according to claim 1, in which the application of the release-controlling shell in step h) is performed by means of air suspension technology.

18. A process according to claim 1, in which the release-controlling shell in step h) is formed by a homopolymer or copolymer containing alpha-hydroxy acid units.

19. A process according to claim 18, in which the alpha-hydroxy acid is lactic acid and/or glycolic acid.

20. A process for converting a water-soluble protein into a concentrated and/or solidified form thereof, which comprises concentrating the water-soluble protein into a highly viscous solution thereof, which has the ability of forming droplets which can be handled at room temperature, or into a precipitation thereof in the form of solid particles, by a mixing of the solution with an aqueous solution of polyethylene glycol (PEG).

21. A process according to claim 20, which is performed in the absence of any freezing or lyophilization operation.

22. A process according to claim 20, which is performed in the absence of any organic solvent.

23. A process according to claim 20, which is performed in the absence of any spraying operation.

24. A process for converting a water-soluble protein into a concentrated and/or solidified form thereof, which comprises mixing as performed as defined in claim 1 an aqueous solution of said protein with an aqueous solution of polyethylene glycol (PEG) under such conditions that the protein is concentrated and/or solidified.

25. The process according to claim 1, in which the polyethylene glycol used in step b) has an average molecular weight of 4,000–35,000 Da.

26. The process according to claim 1, in which the polyethylene glycol used in step b) has an average molecular weight of 6,000–20,000 Da.

27. The process according to claim 1, in which the polyethylene glycol used in step b) has an average molecular weight of about 20,000 Da.

28. The process according to claim 1, in which the concentration of the polyethylene glycol used in step b) is in the range of 2–45% (w/w).

29. The process according to claim 1, in which the concentration of the polyethylene glycol used in step b) is in the range of 10–40% (w/w).

30. The process according to claim 1, in which the concentration of the polyethylene glycol used in step b) is in the range 20–35% (w/w).

31. The process according to claim 1, in which in step d) a biocompatible and biodegradable polymer is utilized, which has an average molecular weight within the range of 1–110 kDA.

32. The process according to claim 11, in which the polyethylene glycol has an average molecular weight of 1–35 kDA.

33. The process according to claim 13, in which the polymer droplets are formed which give the size required for the microparticles as a mean particle diameter.

34. The process according to claim 1, in which in step e) polymer droplets are formed which give the size required for the microparticles, in the dry state, within the range of 20–100 μm.

35. The process according to claim 1, in which in step e) polymer droplets are formed which give the size required for the microparticles, in the dry state, within the range of 20–80 μm.

36. The process of claim 16, wherein the proteins are recombinantly produced proteins.

37. The process according to claim 1, which is performed in the absence of any freezing or lyophilization operation.

38. The process according to claim 1, which is performed in the absence of any organic solvent.

39. The process according to claim 1, which is performed in the absence of any spraying operation.

* * * * *